(12) United States Patent
De Kock et al.

(10) Patent No.: US 10,286,208 B2
(45) Date of Patent: May 14, 2019

(54) FULLY INTEGRATED LEAD STABILIZER FOR MEDICAL ELECTRICAL LEADS AND METHODS OF ATTACHMENT

(71) Applicant: Cardiac Pacemakers, Inc., St. Paul, MN (US)

(72) Inventors: Andrew L. De Kock, Andover, MN (US); Christopher A. Fuhs, Roseville, MN (US); G. Shantanu Reddy, Minneapolis, MN (US); Diana K. Ma, Roseville, MN (US); David A. Durand, Osceola, WI (US); Daniel J. Cooke, Roseville, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 155 days.

(21) Appl. No.: 15/159,707

(22) Filed: May 19, 2016

(65) Prior Publication Data

US 2016/0339233 A1 Nov. 24, 2016

Related U.S. Application Data

(60) Provisional application No. 62/164,023, filed on May 20, 2015.

(51) Int. Cl.
*A61N 1/05* (2006.01)

(52) U.S. Cl.
CPC ............... *A61N 1/057* (2013.01); *A61N 1/05* (2013.01); *A61N 1/059* (2013.01); *A61N 1/0558* (2013.01); *A61N 2001/0582* (2013.01)

(58) Field of Classification Search
CPC ....................................................... A61N 1/057
See application file for complete search history.

(56) References Cited

U.S. PATENT DOCUMENTS

| 4,254,774 A | 3/1981 | Boretos |
| 4,266,552 A | 5/1981 | Dutcher et al. |
| 4,276,882 A | 7/1981 | Dickhudt et al. |
| 4,287,891 A | 9/1981 | Peters |
| 4,301,815 A | 11/1981 | Doring |
| 4,387,727 A | 6/1983 | Sandstrom |

(Continued)

FOREIGN PATENT DOCUMENTS

| EP | 0625359 A2 | 11/1994 |
| EP | 1314449 A2 | 5/2003 |

(Continued)

OTHER PUBLICATIONS

International Search Report and Written Opinion issued in PCT/US2016/033364, dated Oct. 10, 2016, 14 pages.

(Continued)

*Primary Examiner* — Carl H Layno
*Assistant Examiner* — Jennifer L Ghand
(74) *Attorney, Agent, or Firm* — Seager, Tufte & Wickhem LLP

(57) ABSTRACT

Various aspects of the present disclosure are directed toward methods, apparatuses, and systems that include an implantable medical device comprising an implantable lead, a suture sleeve having an interior surface defining a lumen of the suture sleeve that receives the implantable lead, and an engagement feature configured to non-removeably secure the suture sleeve to the implantable lead.

2 Claims, 6 Drawing Sheets

(56) References Cited

U.S. PATENT DOCUMENTS

| | | |
|---|---|---|
| 4,409,994 A | 10/1983 | Doring |
| 4,437,475 A | 3/1984 | White |
| 4,442,840 A | 4/1984 | Wojciechowicz, Jr. |
| 4,516,584 A | 5/1985 | Garcia |
| 4,517,971 A | 5/1985 | Sorbonne |
| 4,519,404 A | 5/1985 | Fleischhacker |
| 4,538,623 A | 9/1985 | Proctor et al. |
| 4,550,737 A | 11/1985 | Osypka |
| 4,553,961 A | 11/1985 | Pohndorf et al. |
| 4,585,013 A | 4/1986 | Harris |
| 4,613,329 A | 9/1986 | Bodicky |
| 4,615,472 A | 10/1986 | Nash |
| 4,672,979 A | 6/1987 | Pohndorf |
| 4,676,782 A | 6/1987 | Yamamoto et al. |
| 4,683,895 A | 8/1987 | Pohndorf |
| 4,768,523 A | 9/1988 | Cahalan et al. |
| 4,796,643 A | 1/1989 | Nakazawa et al. |
| 4,906,233 A | 3/1990 | Moriuchi et al. |
| 5,036,862 A | 8/1991 | Pohndorf |
| 5,107,856 A | 4/1992 | Kristiansen et al. |
| 5,129,405 A | 7/1992 | Milijasevic et al. |
| 5,152,298 A | 10/1992 | Kreyenhagen et al. |
| 5,242,431 A | 9/1993 | Kristiansen |
| 5,257,975 A | 11/1993 | Foshee |
| 5,273,053 A | 12/1993 | Pohndorf |
| 5,366,496 A | 11/1994 | Dahl et al. |
| 5,376,108 A | 12/1994 | Collins et al. |
| 5,423,763 A | 6/1995 | Helland et al. |
| 5,476,493 A | 12/1995 | Muff |
| 5,484,445 A | 1/1996 | Knuth |
| 5,549,619 A | 8/1996 | Peters et al. |
| 5,583,319 A | 12/1996 | Lieurance |
| 5,584,874 A | 12/1996 | Rugland et al. |
| 5,603,730 A | 2/1997 | Romkee |
| 5,628,780 A | 5/1997 | Helland et al. |
| 5,674,273 A | 10/1997 | Helland |
| 5,683,403 A | 11/1997 | Adams et al. |
| 5,683,446 A | 11/1997 | Gates |
| 5,709,644 A | 1/1998 | Bush |
| 5,735,891 A | 4/1998 | White |
| 5,746,722 A | 5/1998 | Pohndorf et al. |
| 5,800,402 A | 9/1998 | Bierman |
| 5,824,032 A | 10/1998 | Belden |
| 5,827,296 A | 10/1998 | Morris et al. |
| 5,843,146 A | 12/1998 | Cross, Jr. |
| 5,871,528 A | 2/1999 | Camps et al. |
| 5,876,429 A | 3/1999 | Schroeppel |
| 5,957,968 A | 9/1999 | Belden et al. |
| 6,002,969 A | 12/1999 | Machek et al. |
| 6,134,477 A | 10/2000 | Knuteson |
| 6,173,206 B1 | 1/2001 | Shchervinsky |
| 6,178,356 B1 | 1/2001 | Chastain et al. |
| 6,188,932 B1 | 2/2001 | Lindegren |
| 6,259,953 B1 | 7/2001 | Lucchesi et al. |
| 6,463,334 B1 | 10/2002 | Flynn et al. |
| 6,473,654 B1 | 10/2002 | Chinn |
| 6,554,802 B1 | 4/2003 | Pearson et al. |
| 6,592,553 B2 | 7/2003 | Zhang et al. |
| 6,643,550 B2 | 11/2003 | Westlund et al. |
| 6,895,277 B2 | 5/2005 | Westlund et al. |
| 6,901,287 B2 | 5/2005 | Davis et al. |
| 6,912,423 B2 | 6/2005 | Ley et al. |
| 6,915,169 B2 | 7/2005 | Flynn et al. |
| 6,921,295 B2 | 7/2005 | Sommer et al. |
| 6,985,777 B2 | 1/2006 | Tsuboi et al. |
| 7,082,337 B2 | 7/2006 | Sommer et al. |
| 7,090,660 B2 | 8/2006 | Robert et al. |
| 7,184,841 B1 * | 2/2007 | Bodner ............... A61N 1/057 607/122 |
| 7,218,972 B2 | 5/2007 | Rodriguez |
| 7,242,986 B2 | 7/2007 | Rodriguez |
| 7,248,930 B1 | 7/2007 | Woloszko et al. |
| 7,398,125 B2 | 7/2008 | Osypka et al. |
| 7,747,334 B2 | 6/2010 | Bly et al. |
| 7,765,015 B2 | 7/2010 | Johnson et al. |
| 7,806,886 B2 | 10/2010 | Kanderian, Jr. et al. |
| 7,914,582 B2 | 3/2011 | Felt et al. |
| 7,933,661 B2 | 4/2011 | Erlebacher |
| 8,000,811 B2 | 8/2011 | Hill |
| 8,126,569 B2 | 2/2012 | Rivard et al. |
| 8,271,096 B2 | 9/2012 | Rivard et al. |
| 8,774,942 B2 | 7/2014 | Lund et al. |
| 8,954,165 B2 | 2/2015 | Sharma et al. |
| 9,216,563 B2 * | 12/2015 | Barner ............... A61N 1/0558 |
| 9,486,622 B2 | 11/2016 | Clark et al. |
| 2002/0133121 A1 | 9/2002 | Bierman |
| 2003/0050668 A1 | 3/2003 | Lee |
| 2003/0100937 A1 | 5/2003 | Tsuboi et al. |
| 2003/0130616 A1 | 7/2003 | Steil et al. |
| 2003/0195600 A1 | 10/2003 | Tronnes et al. |
| 2003/0220678 A1 | 11/2003 | Tronnes et al. |
| 2004/0059403 A1 | 3/2004 | Massullo |
| 2004/0093052 A1 | 5/2004 | Westlund et al. |
| 2004/0143216 A1 | 7/2004 | Douglas et al. |
| 2004/0199233 A1 | 10/2004 | Rodriguez |
| 2004/0254623 A1 | 12/2004 | Rodriguez et al. |
| 2005/0080470 A1 | 4/2005 | Westlund et al. |
| 2005/0137664 A1 | 6/2005 | Sommer et al. |
| 2005/0177220 A1 | 8/2005 | Iaizzo et al. |
| 2005/0202703 A1 | 9/2005 | Westlund et al. |
| 2005/0267557 A1 | 12/2005 | Flynn et al. |
| 2006/0235484 A1 | 10/2006 | Jaax et al. |
| 2006/0264803 A1 | 11/2006 | Lui et al. |
| 2007/0078399 A1 | 4/2007 | Olson |
| 2007/0156216 A1 | 7/2007 | McAuliffe et al. |
| 2007/0225784 A1 | 9/2007 | Bly et al. |
| 2007/0282412 A1 | 12/2007 | Soltis et al. |
| 2007/0282414 A1 | 12/2007 | Soltis et al. |
| 2007/0282415 A1 | 12/2007 | Tockman et al. |
| 2007/0293922 A1 | 12/2007 | Soltis et al. |
| 2008/0228251 A1 | 9/2008 | Hill |
| 2008/0262587 A1 | 10/2008 | Flynn et al. |
| 2008/0262588 A1 | 10/2008 | Zarembo et al. |
| 2009/0125058 A1 | 5/2009 | Bodner et al. |
| 2009/0125059 A1 | 5/2009 | Verzal et al. |
| 2009/0125060 A1 | 5/2009 | Rivard et al. |
| 2009/0125061 A1 | 5/2009 | Rivard et al. |
| 2009/0326473 A1 | 12/2009 | Rosenberg et al. |
| 2010/0016801 A1 | 1/2010 | Rosenberg et al. |
| 2010/0114034 A1 | 5/2010 | Wright et al. |
| 2010/0174240 A1 * | 7/2010 | Wells ............... A61N 1/0558 604/175 |
| 2011/0009935 A1 | 1/2011 | Kane et al. |
| 2011/0046669 A1 | 2/2011 | Goraltchouk et al. |
| 2011/0054581 A1 | 3/2011 | Desai et al. |
| 2012/0029335 A1 | 2/2012 | Sudam et al. |
| 2012/0071959 A1 | 3/2012 | Helgesson |
| 2012/0150202 A1 | 6/2012 | Chen et al. |
| 2012/0330354 A1 | 12/2012 | Kane et al. |
| 2012/0330355 A1 | 12/2012 | Finley et al. |
| 2013/0138200 A1 | 5/2013 | Mayberry et al. |
| 2013/0158640 A1 | 6/2013 | Soltis et al. |
| 2014/0121739 A1 | 5/2014 | Fuhs et al. |
| 2014/0128948 A1 | 5/2014 | Clark et al. |
| 2015/0005856 A1 | 1/2015 | Pianca et al. |
| 2015/0045865 A1 | 2/2015 | Nageri et al. |
| 2015/0051675 A1 | 2/2015 | Barner |
| 2015/0352352 A1 | 12/2015 | Soltis et al. |

FOREIGN PATENT DOCUMENTS

| | | |
|---|---|---|
| EP | 2275169 A1 | 1/2011 |
| JP | H06505190 A | 6/1994 |
| JP | 2003047653 A | 2/2003 |
| JP | 2003220148 A | 8/2003 |
| JP | 2014506504 A | 3/2014 |
| WO | WO9833551 A1 | 8/1998 |
| WO | WO9848880 A1 | 11/1998 |
| WO | WO02064206 A2 | 8/2002 |
| WO | WO03086532 A1 | 10/2003 |
| WO | WO03099375 A2 | 12/2003 |
| WO | 2004028345 A2 | 4/2004 |

(56) References Cited

FOREIGN PATENT DOCUMENTS

| WO | 2005061047 A1 | 7/2005 |
|---|---|---|
| WO | WO2006116454 A2 | 11/2006 |
| WO | WO2007024164 A1 | 1/2007 |

OTHER PUBLICATIONS

International Search Report and Written Opinion issued in PCT/US2013/067138, dated Mar. 20, 2014, 13 pages.
Invitation to Pay Additional Fees and Partial international Search issued in PCT/US2016/033364, dated Aug. 10, 2016, 6 pages.
Pacing Lead Stabilizer with Modified Slit Geometry, Technical Disclosure from www.ip.com, No. IPCOM000130753D, published Nov. 3, 2005, full document available at http://www.ip.com/pubview/IPCOM000125732D,6 pages.
PCT Invitation to Pay Additional Fees and Partial Search Report issued in PCT/US2016/033364 dated Aug. 10, 2016, 6 pages.
Suture Sleeve with Removable Fins, Technical Disclosure from www.ip.com, No. IPCOM000125732D, published Jun. 15, 2005, full document available at http://www.ip.com/pubview/IPCOM000125732D, 4 pages.

* cited by examiner ically rely on an implantable
FULLY INTEGRATED LEAD STABILIZER FOR MEDICAL ELECTRICAL LEADS AND METHODS OF ATTACHMENT

CROSS-REFERENCE TO RELATED APPLICATION

This application claims priority to Provisional Application No. 62/164,023, filed May 20, 2015, which is herein incorporated by reference in its entirety.

TECHNICAL FIELD

The present disclosure relates generally to implantable medical leads. More specifically, the disclosure relates to a suture sleeve for an implantable medical lead assembly.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of an implantable pulse generator (IPG) such as a pacemaker, an implantable cardioverter defibrillator (ICD), a cardiac resynchronization (CRT) device, or a subcutaneous implantable cardioverter defibrillator. Such devices typically rely on an implantable lead to convey electrical signals between the IPG and the heart. An implantable lead can additionally or alternatively be used to stimulate other nervous and/or musculature systems of the body. Whether for a cardiac lead or for a lead used elsewhere in the body, a suture sleeve can be provided along the lead to anchor the lead.

SUMMARY

In Example 1, an implantable medical device comprising an implantable lead having a distal region, a proximal region, and an intermediate region therebetween; a suture sleeve having an interior surface defining a lumen of the suture sleeve, the lumen receiving the implantable lead, the suture sleeve comprising an exterior surface that defines at least one suture receiving track; and an engagement feature arranged on the implantable lead and configured to non-removeablely secure the suture sleeve to the implantable lead.

In Example 2, the medical device of Example 1, wherein the suture sleeve comprises silicone and the implantable lead comprises polycarbonate.

In Example 3, the medical device of Examples 1 or 2, wherein the engagement feature comprises an adhesive layer.

In Example 4, the medical device of Example 3, wherein the adhesive layer comprises first durometer and the suture sleeve comprises a second durometer.

In Example 5, the medical device of Example 4, wherein the first durometer is lower than the second durometer.

In Example 6, the medical device of Example 1, wherein the suture sleeve further comprises at least one indentation along the interior surface of the suture sleeve, and the engagement feature comprises at least one radial projection comprising an upper surface, a lower surface, and sidewalls, the upper surface and the sidewalls being configured to provide a mechanical stop for the suture sleeve and engage the at least one indentation to secure the suture sleeve to the implantable lead.

In Example 7, the medical device of Example 6, wherein the at least one radial projection comprises opposing sidewalls configured to engage the at least one indentation to secure the suture sleeve to the implantable lead.

In Example 8, the medical device of Example 1, wherein the suture sleeve further comprises at least one cavity along the interior surface of the suture sleeve, and the engagement feature comprises at least one radial projection having rivets configured to engage a top surface of the suture sleeve on either side of the at least one cavity to secure the suture sleeve to the implantable lead.

In Example 9, the medical device of any of the Examples 1-8, further comprising at least one electrode secured in the distal region of the implantable lead.

In Example 10, a method for securing a suture sleeve to an implantable lead having a distal region, a proximal region, and an intermediate region therebetween, the method comprising: forming a suture sleeve having an interior surface defining a lumen of the suture sleeve, the lumen receiving the implantable lead, the suture sleeve comprising an exterior surface that defines at least one suture receiving track; forming an engagement feature on an exterior surface of the implantable lead; and securing the suture sleeve to the implantable lead by engaging the suture sleeve with the engagement feature In Example 11, the method of Example 10, wherein forming the engagement feature comprises providing an adhesive between the suture sleeve and the exterior surface of the medical lead.

In Example 12, the method of Example 10, wherein forming the engagement feature comprises attaching at least one radial projection to the implantable lead, the at least one radial projection, and securing the suture sleeve to the implantable lead comprising engaging the suture sleeve with the at least one radial projection.

In Example 13, the method of Example 10, wherein the at least one radial projection comprises a first radial projection and a second radial projection, and wherein securing the suture sleeve to the implantable lead comprises securing the suture sleeve between the first radial projection and the second radial projection.

In Example 14, the method of Examples 10, 11, or 12, wherein securing the suture sleeve to the implantable lead comprises at least one of over-molding, pre-molding, or heat bonding the suture sleeve to the implantable lead.

In Example 15, the method of Example 10, further comprising plasma treating the implantable lead prior to forming the engagement feature on the exterior surface of the implantable lead.

In Example 16, an implantable medical device comprising: an implantable lead having a distal region, a proximal region, and an intermediate region therebetween; a suture sleeve having an interior surface defining a lumen of the suture sleeve, the lumen receiving the implantable lead, the suture sleeve comprising an exterior surface that defines at least one suture receiving track; and an engagement feature arranged on the implantable lead and configured to non-removeablely secure the suture sleeve to the implantable lead.

In Example 17, the medical device of Example 16, wherein the suture sleeve comprises silicone and the implantable lead comprises polycarbonate.

In Example 18, the medical device of Example 16, wherein the engagement feature comprises an adhesive layer.

In Example 19, the medical device of Example 18, wherein the adhesive layer comprises a first durometer and the suture sleeve comprises a second durometer.

In Example 20, the medical device of Example 18, wherein the first durometer is lower than the second durometer.

In Example 21, the medical device of Example 16, wherein the suture sleeve further comprises at least one indentation along the interior surface of the suture sleeve, and the engagement feature comprises at least one radial projection having an upper surface, a lower surface, and sidewalls, the upper surface and the sidewalls being configured to provide a mechanical stop for the suture sleeve and engage the at least one indentation to secure the suture sleeve to the implantable lead.

In Example 22, the medical device of Example 21, wherein the at least one radial projection comprises opposing sidewalls configured to engage the at least one indentation to secure the suture sleeve to the implantable lead.

In Example 23, the medical device of Example 16, wherein the suture sleeve further comprises at least one cavity along the interior surface of the suture sleeve, and the engagement feature comprises at least one radial projection comprising rivets configured to engage a top surface of the suture sleeve on either side of the at least one cavity to secure the suture sleeve to the implantable lead.

In Example 24, an implantable medical device comprising: an implantable lead having a distal region, a proximal region, and an intermediate region therebetween; an electrode arranged at the distal region of the implantable lead and configured to provide a stimulation pulse to a patient's heart; a suture sleeve having an interior surface defining a lumen of the suture sleeve, the lumen receiving the implantable lead, the suture sleeve comprising an exterior surface that defines at least one suture receiving track and at least one indentation along the interior surface of the suture sleeve; a sense electrode between the electrode and the suture sleeve; and at least one radial projection configured engage the at least one indentation to secure the suture sleeve to the implantable lead.

In Example 25, the medical device of Example 24, wherein a gap between the suture sleeve and the sense electrode is between 2 mm and 15 mm.

In Example 26, the medical device of Example 24, further comprising a second sense electrode at a distal tip of the implantable lead.

In Example 27, the medical device of Example 24, wherein the electrode is configured to provide an electrical stimulation to a patient's heart.

In Example 28, the medical device of Example 24, wherein the exterior surface of the suture sleeve comprises a surface roughness of between 45 and 75 Ra.

In Example 29, the medical device of Example 24, wherein the suture sleeve comprises silicone and the at least one radial projection comprises at least one of polycin vorite (PCV), polyurethane, and polycarbonate.

In Example 30, a method for securing a suture sleeve to an implantable lead having a distal region, a proximal region, and an intermediate region therebetween, the method comprising: forming a suture sleeve having a lumen defining an interior surface of the suture sleeve and sized to receive an implantable lead, the suture sleeve being arranged at the distal region of the implantable lead and comprising at least one suture receiving track on an exterior surface of the suture sleeve; forming an engagement feature on an exterior surface of the implantable lead; and securing the suture sleeve to the implantable lead by engaging the suture sleeve with the engagement feature In Example 31, the method of Example 30, wherein forming the engagement feature comprises providing an adhesive between the suture sleeve and the exterior surface of the medical lead.

In Example 32, the method of Example 30, wherein forming the engagement feature comprises attaching at least one radial projection to the implantable lead, the at least one radial projection, and securing the suture sleeve to the implantable lead comprises engaging the suture sleeve with the at least one radial projection.

In Example 33, the medical device of Example 32, wherein the at least one radial projection comprises a first radial projection and a second radial projection, and wherein securing the suture sleeve to the implantable lead comprising the securing the suture sleeve between the first radial projection and the second radial projection.

In Example 34, the method of Example 30, wherein securing the suture sleeve to the implantable lead comprises at least one of over-molding, pre-molding, or heat bonding the suture sleeve to the implantable lead.

In Example 35, the method of Example 30, further comprising plasma treating the implantable lead implantable lead prior to forming the engagement feature on the exterior surface of the implantable lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
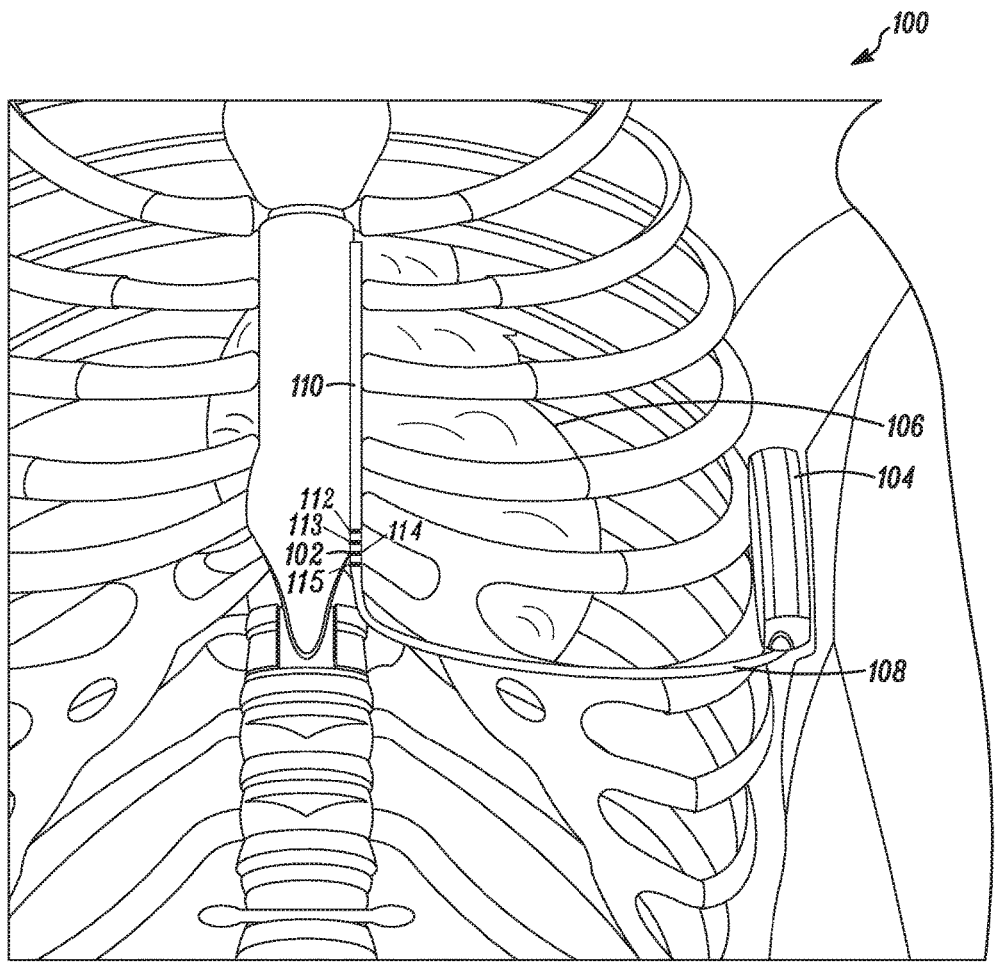
FIG. 1A shows an implantable medical system including a suture sleeve as implanted in a patient.

While the full scope of this disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1A shows an implantable medical system 100. The implanted medical system 100 includes a pulse generator 104 implanted within a patient. As shown, the pulse generator 104 can be connected to an implantable lead 108. FIG. 1A shows the implantable medical system 100 arranged for delivering electrical stimulation to the heart 106. The particular implantable medical system 100 shown is implanted subcutaneously along the patient's chest or abdomen, however other implant locations are possible. As shown in FIG. 1A, the pulse generator 104 and the implantable lead 108 are implanted at an implant location that is outside of the ribcage. In various embodiments, the pulse generator 104 is a pacemaker, an implantable cardioverter/defibrillator (ICD), a cardiac resynchronization (CRT) device, a subcutaneous implantable cardioverter defibrillator, a neurostimulator, or any other implantable medical device for delivering a therapy, and may be configured to deliver one or more of pacing, CRT, defibrillation, and neurostimulation therapies, amongst other options. The pulse generator 104 may additionally or alternatively be configured for sensing within the body, such as sensing bioelectrical signals and/or other physiological parameters.

The entirety of the implantable lead 108 is implanted subcutaneously, but outside of the ribcage. As such, in various embodiments, no part of the implantable lead 108 comes into contact with the heart. In some other embodiments, at least part of the implantable lead 108 may extend into the ribcage, such as to make contact with the heart.

One or more portions of the implantable lead 108 may be secured in place with a suture sleeve 102. The suture sleeve 102 can be secured to the implantable lead 108 prior to beginning surgery, such as in manufacturing of the implantable lead 108 without involvement of a surgeon or other medical professional. Securing the suture sleeve 102 to the implantable lead 108 during manufacturing may allow for a more efficient implantation procedure as a surgeon or trained medical professional would not have to position the suture sleeve 102 on the implantable lead 108 while operating. Further, securing the suture sleeve 102 to the implantable lead 108 in this manner may also provide for an accurate and defined arrangement of the suture sleeve 102 on the implantable lead 108.

The implantable lead 108 can include an electrode 110. The electrode 110 shown in FIG. 1A is a defibrillation electrode having a large surface area. Additionally or alternatively, smaller pace and/or sense electrodes, such as ring electrodes, can be deposed on the implantable lead 108. While a single electrode 110 is shown, it will be understood that a greater number of electrodes and/or different types of electrodes can be provided on the implantable lead 108. The flexible lead body can be formed from a polymeric tube.

In various embodiments, the implantable lead 108 is inserted into the patient through a first incision (entry site) formed in the side of the patient. A stiff tube (e.g., an introducer, not shown) can be inserted into and through the first incision and the implantable lead 108 can be moved through the tube toward the sternum of the patient. A second incision can be made near an upper portion of the sternum of the patient. The second incision can allow for an access point for a physician to position the distal end of the implantable lead 108. In addition, a third incision can be made near a lower portion of the sternum. The third incision allows for access to the suture sleeve 102, which is provided to secure the implantable lead 108 in place. Other suitable access sites may be utilized in various other embodiments, and the incisions may be made in any order. Once the suture sleeve 102 is appropriately positioned, the physician may secure the implantable lead 108 in place by tying sutures 112, 113, 114, 115 to the suture sleeve 102, and threading the sutures 112, 113, 114, 115 within the body.

Figure 1B:
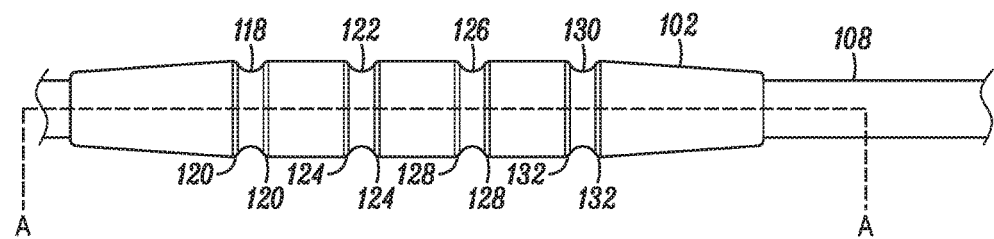
FIG. 1B shows an enlarged schematic illustration the suture sleeve of FIG. 1A.

FIG. 1B shows an enlarged schematic illustration of the suture sleeve 102 of FIG. 1A. The suture sleeve 102 includes a lumen (and other internal components) that defines an interior surface of the suture sleeve. The lumen and the implantable lead 108 are sized relative to one another such that the implantable lead 108 can be received within the lumen of the suture sleeve 102. An exterior surface of the suture sleeve 102 can include one or more receiving tracks 118, 122, 126, 130. Each track 118, 122, 126, 130 can be defined by opposing sidewalls 120, 124, 128, 132. The sidewalls 120, 124, 128, 132 can hold a suture within the suture receiving track 118, 122, 126, 130 to minimize movement between the suture and the suture sleeve 102. While four tracks 118, 122, 126, 130 are shown in the embodiment of FIG. 1B, it will be understood that no tracks, a single track, two tracks, three tracks, or any number of tracks can alternatively be provided. One or more sutures can be placed within each track 118, 122, 126, 130 during an implantation procedure to secure the implantable lead 108 in place within the body. Each suture (as shown above with reference to FIG. 1A) can also penetrate and/or loop around tissue to secure the suture sleeve 102 to the tissue. A knot can be tied in each suture after the suture is wrapped around the suture sleeve 102. The suture sleeve 102 can prevent the sutures from contacting the lead 108 to prevent damaging the implantable lead 108 while also securing the lead 108 at an implant site. Further, in certain embodiments, the suture sleeve 102 can have a surface roughness of between 45 and 75 Ra to enhance securement of the suture with the suture sleeve 102.

The suture sleeve 102 can be formed from polymeric material, such as silicone. The material of the suture sleeve 102 may not include properties that allow for heat welding or chemical bonding of the suture sleeve 102 to the implantable lead 108. Silicone, for example, may not readily adhere to other materials. However, it is advantageous to form the suture sleeve 102 of silicone, or like materials, due to the biocompatible and robust properties of silicone and similar materials. The suture sleeve 102 may be non-removeably secured to the implantable lead 108 via one or more features as further discussed herein.

Figure 2A:
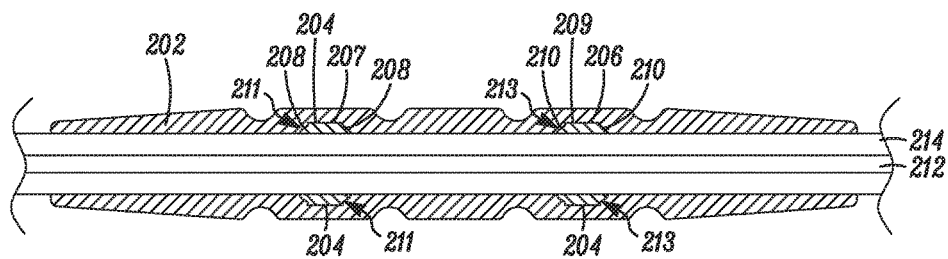
FIG. 2A shows a cross sectional view, taken from FIG. 1B, of a suture sleeve secured to an implantable by radial projections.

FIG. 2A shows an enlarged cross sectional view of a suture sleeve 202 secured to an implantable lead 214 by radial projections 204, 206. The cross sectional view can represent, for example, a cross-sectional view taken from the line A-A shown in FIG. 1B. The cross-sectional view in FIG.

2A shows the cross-sectional aspects of the suture sleeve 202 and a lumen 212 of the implantable lead 214, however, the other internal components (e.g., electrical components) of the implantable lead 214 are omitted. The suture sleeve 202 is mounted on an implantable lead 214. The suture sleeve 202 is secured to the implantable lead 214 by one or more radial projections 204, 206. The radial projections 204, 206 may be a continuous ring around the implantable lead 214 (as is shown in FIG. 1B), or, the radial projections 204, 206 may be only on portions of the implantable lead 214. The radial projection 204, 206 can have sidewalls 208, 210 that bound an upper surface 207, 209 of the radial projections 204, 206.

The suture sleeve 202 can also include one or more indentations 211, 213. The one or more indentations 211, 213 may be the opposite (e.g., mirror) of the structure of the radial projections 204, 206 and interface therewith. The sidewalls 210 can be curved such that differentiation between the upper surface 207, 209 of the radial projections 204, 206 are gradually formed. Further, the sidewalls 208, 210 can be formed at a steeper angle (e.g., 90 degrees) with respect to the upper surface 207, 209. In either instance, the indentations 211, 213 can be provided along the interior surface the suture sleeve 202, and can be complementary to the radial projections 204, 206. The raised profile of the radial projections 204, 206 shown in FIG. 2A provides a mechanical stop for the suture sleeve 202, and the radial projections 204, 206 engage the one or more indentations 211, 213 to secure the suture sleeve 202 to an implantable lead 214.

As noted above with reference to FIG. 1B, the radial projections 204, 206 are provided on an implantable lead 214. The suture sleeve 202 can be secured thereto by sliding the suture sleeve 202 along the implantable lead 214 until the encountering the radial projections 204, 206. The suture sleeve 202 is forced over the radial projections 204, 206, and slid further along the implantable lead 214 until the radial projections 204, 206 engages the indentations 211, 213. If more than one radial projections 204, 206 is provided, the suture sleeve 202 is forced further along the implantable lead 214 until each of the radial projections 204, 206 is provided within the counterpart indentations 211, 213. As noted above, the radial projections 204, 206 can be formed around the entire circumference of the implantable lead 214. In this manner, during manufacturing, the suture sleeve 202 may be slid along the body of the implantable lead 214, and the radial projections 204, 206 will engage the indentations 211, 213 regardless of the rotational positioning of the suture sleeve 202. The indentations 211, 213 may be formed within the suture sleeve 202 prior to placing the suture sleeve 102 on the suture sleeve, or the indentations may be formed as a result of placing the suture sleeve 102 over the respective radial projections 204, 206. The indentations 211, 213 may be formed as a ring-like indentation along the entire interior circumference of the suture sleeve 202.

Figure 2B:
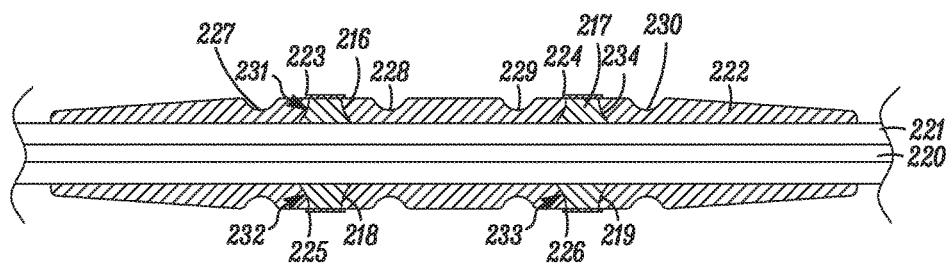
FIG. 2B shows an enlarged cross sectional view, taken from FIG. 1B as an alternative embodiment to that of FIG. 2A, of an attachment mechanism having rivets for securing the suture sleeve to a lead.

FIG. 2B shows an enlarged cross sectional view of a fixation feature for securing a suture sleeve 222 to an implantable lead 221. The cross sectional view can represent, for example, a cross-sectional view taken from the line A-A shown in FIG. 1B. The cross-sectional view in FIG. 2B shows the cross-sectional aspects of the suture sleeve 222 and a lumen 220 of the implantable lead 221, however, the other internal components (e.g., electrical components) of the implantable lead 221 are omitted. The suture sleeve 222 can be secured to the implantable lead 221 by one or more radial projections 216, 217, 218, 219. Each radial projection 216, 217, 218, 219 can include a rivet 223, 224, 225, 226.

Figure 2C:
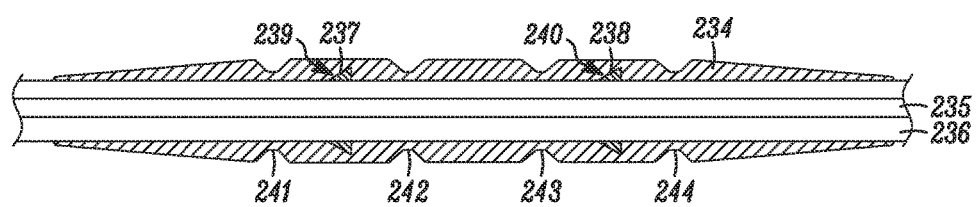
FIG. 2C shows a cross sectional view, taken from FIG. 1B as an alternative embodiment to those of FIGS. 2A-B, of a suture sleeve secure to a lead by a snap-fit mechanism.

An upper surface of the rivets 223, 224, 225, 226 can be substantially parallel with a top surface of the suture sleeve 222. In other instances, an upper surface of the rivets 223, 224, 225, 226 may be provided such that portions thereof on top of a top surface of the suture sleeve 222. The rivet 223, 224, 225, 226 can project axially outward from the radial projections 216, 217, 218, 219 such that a top surface of the rivets 223, 224, 225, 226 are parallel (or substantially parallel and/or angled) relative to an upper surface of the suture sleeve 222. The suture sleeve 222 can wedge between the rivets 223, 224, 225, 226 and a main body portion of the radial projections 216, 217, 218, 219. In addition, the suture sleeve 222 can include indentations 231, 232, 233, 233 (or cavity) that are formed in portions of or as a ring-like indentation/cavity along the entire interior circumference of the suture sleeve 222. In instances where the suture sleeve 222 includes one or more cavities, the suture sleeve 222 may first be placed on the implantable lead 221. Once the suture sleeve 222 is in the desired location along the implantable lead 221, the radial projections 216, 217, 218, 219 can be formed on the implantable lead 221. In this manner, the rivets 223, 224, 225, 226 can be provided along the outside surface of the suture sleeve 222 and hold the suture sleeve 222 against the implantable lead 221. In instances where the suture sleeve 222 includes a plurality of indentations 231, 232, 233, 233, an equal number of the radial projections 216, 217, 218, 219 will also be provided to secure the suture sleeve 222 to the implantable lead 221. In addition, the suture sleeve 222 may include suture one or more receiving tracks 227, 228, 229, 230 that may hold a suture to secure the implantable lead 221 in place within the body FIG. 2C shows a cross sectional view of a snap-fit mechanism for securing a suture sleeve 234 to an implantable lead 236. The cross sectional view can represent, for example, a cross-sectional view taken from the line A-A shown in FIG. 1B. The cross-sectional view in FIG. 2C shows the cross-sectional aspects of the suture sleeve 234 and a lumen 235 of the implantable lead 236, however, the other internal components (e.g., electrical components) of the implantable lead 236 are omitted. The implantable lead 236 can include one or more radial projections 237, 238 that can be bonded to the implantable lead 236. As shown, the radial projections 237, 238 are formed as a continuous ring around the circumference of the implantable lead 236. Indentations 239, 240 in the suture sleeve 234 can be formed complementary to the radial projections 237, 238 to receive the radial projections 237, 238. Similar to the radial projections 237, 238, the indentations 239, 240 are formed as a continuous ring. The radial projections 237, 238 can be snap-fit with the indentations 239, 240 in the inner surface of the implantable lead 236 as a mechanism to secure the suture sleeve 234 to the implantable lead 236.

The radial projections 237, 238 and the indentations 239, 240 may be formed from the same material (e.g., polyurethane or polycarbonate). The suture sleeve 234 may be formed as an upper and lower portion, and guided onto the rivets 226. Thus, in securing the suture sleeve 234 to the implantable lead 236, as is shown in FIG. 2C, the suture sleeve 234 is snapped onto the radial projections 237, 238 such that the indentations 239, 240 and the radial projections 237, 238 are matched. In addition, the suture sleeve 234 may include one or more receiving tracks 241, 242, 243, 244 that may hold a suture to secure the implantable lead 236 in place within the body. The tracks 241, 242, 243, 244 may be formed as a continuous ring around the exterior surface of the suture sleeve 234.

Figure 2D:
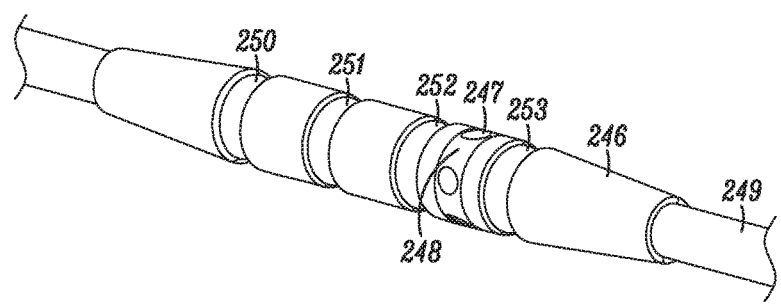
FIG. 2D shows a schematic illustration of a suture sleeve secured to a lead by a securement ring.

FIG. 2D shows a schematic illustration of a suture sleeve 246 and radial projection 247 having a securement ring 248. The radial projection 247 shown in FIG. 2D is a single structure arranged that includes the securement ring 248. As shown in FIG. 2D, the suture sleeve 246 includes two portions 254, 255 on either side of the securement ring 248. Similar to the example shown in FIG. 2B, the securement ring 248 can include an adhesive to secure the suture sleeve 246 to an implantable lead 249. The securement ring 248 can contact both portions 254, 255 of the suture sleeve 246 via the securement ring 248, and secure the suture sleeve 246 to the implantable lead 249. The radial projection 247 and the securement ring 248 may be bonded together. The radial projection 247 may be secured to the implantable lead 249, and secured to the securement ring 248. The securement ring 248 secures the suture sleeve 246 to the radial projection 247. The radial projection 247 may be secured to the implantable lead 249 by first plasma treating the implantable lead 2479, and subsequently bonding the radial projection 247 thereto. In addition, the suture sleeve 246 may include suture one or more receiving tracks 250, 251, 252, 253 that may hold a suture to secure the implantable lead 249 in place within the body. The tracks 250, 251, 252, 253 may be formed as a continuous ring around the exterior surface of the suture sleeve 246.

Figure 2E:
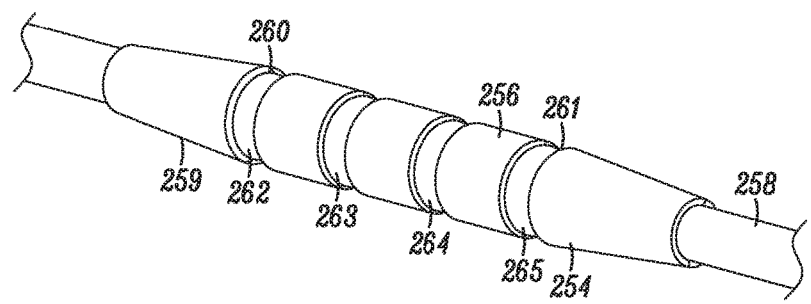
FIG. 2E shows a schematic illustration of a suture sleeve secure to a lead by radial projection having end portions.

FIG. 2E shows a schematic illustration of a suture sleeve 256 and radial projection having end portions 259. The end portions 259 can be provided on either side of the suture sleeve 256 to secure the suture sleeve 256 to an implantable lead 258. End edges 260, 261 of the end portions 259 can overlap portions of the suture sleeve 256, or can be provided such that the end edges 260, 261 of the end portions 259 contact the edges of the suture sleeve 256. During manufacturing of, the suture sleeve 256 may be positioned on the implantable lead 258. Prior to or after position the suture sleeve 256 on the implantable lead 258, the end portions 259 may be secured on the implantable lead 258 and the edges 260, 261 will engage portions of the suture sleeve 256 to secure the suture sleeve 256 to the implantable lead 258. In addition, the suture sleeve 256 may include suture one or more receiving tracks 262, 263, 264, 265 that may hold a suture to secure the implantable lead 258 in place within the body. The tracks 262, 263, 264, 265 may be formed as a continuous ring around the exterior surface of the suture sleeve 256.

Figure 2F:
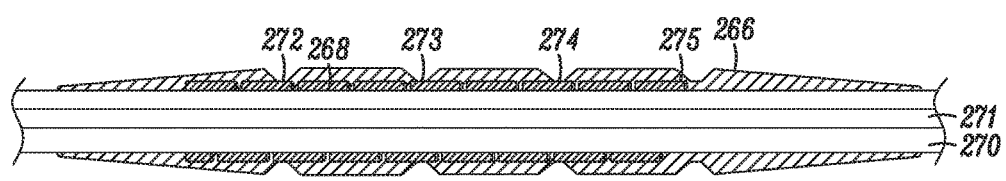
FIG. 2F shows a cross sectional view, taken from FIG. 1B as an alternative embodiment to those of FIGS. 2A-C, of a suture sleeve secured to a lead by a plurality of radial projections for securing the suture sleeve to an implantable lead.

FIG. 2F shows a cross sectional view, taken from FIG. 1B, of a suture sleeve 266 and a plurality of radial projections 268 for securing the suture sleeve 266 to an implantable lead 270. The cross sectional view can represent, for example, a cross-sectional view taken from the line A-A shown in FIG. 1B. The cross-sectional view in FIG. 2F shows the cross-sectional aspects of the suture sleeve 266 and a lumen 271 of the implantable lead 270, however, the other internal components (e.g., electrical components) of the implantable lead 270 are omitted. The plurality of radial projections 268 can be formed as part of a single material that is notched for flexibility. The plurality of radial projections 268 are bonded to the implantable lead 270, and the suture sleeve 266 can be provided over the plurality of radial projections 268. The radial projections 268 can be secured directly to the implantable lead 270. In addition, the radial projections 268 may be heat bonded to the implantable lead 270, or secured by other methods of discussed herein. In addition, the suture sleeve 266 may include suture one or more receiving tracks 272, 273, 274, 275 that may hold a suture to secure the implantable lead 270 in place within the body. The tracks 272, 273, 274, 275 may be formed as a continuous ring around the exterior surface of the suture sleeve 266.

Figure 2G:
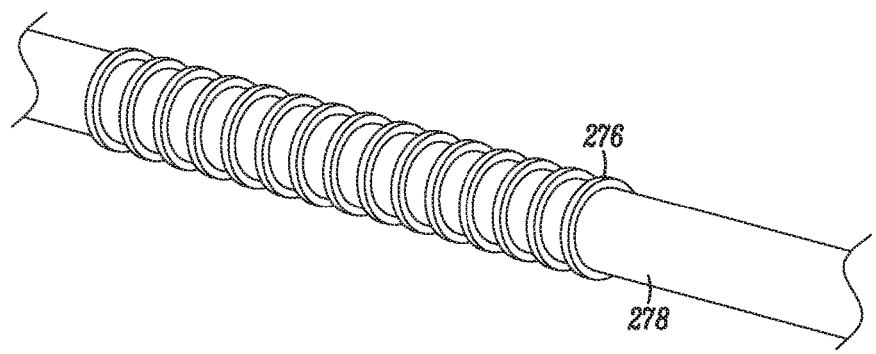
FIG. 2G shows a schematic illustration of a radial projection having a ring configuration.
Figure 2H:
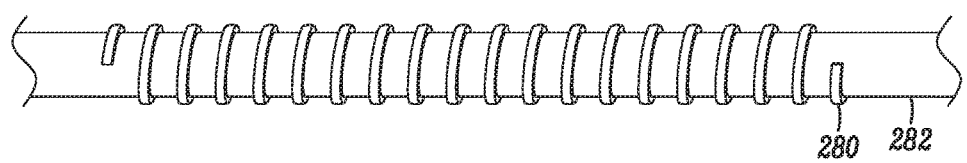
FIG. 2H shows a schematic illustration of a radial projection having a spiral configuration.

FIG. 2G shows a schematic illustration of a radial projection 276 having a circular configuration. The radial projection 276 shown in FIG. 2G can also be formed of a single piece of material. A suture sleeve (not shown) can be secured to an implantable lead 278 by bonding or otherwise securing the suture sleeve over the radial projection 276. Due to the circular configuration of the radial projection 276, the suture sleeve can be provided with suture receiving tracks, such as those shown and discussed above with reference to FIG. 1B, via the securement of a suture sleeve over the radial projection 276. The radial projection 276 can have a notched configuration that can be used in relation to embodiments of the present invention. In certain embodiments, the circular shape can be provided with a taper. The taper can occur from both ends of the radial projection 276 such that the centermost portion is raised apart from the implantable lead 278 as compared to the end portions of the radial projection 247. FIG. 2H shows a schematic illustration of radial projection 280 having a spiral configuration. The radial projection 280 shown in FIG. 2H may be formed of a single piece of material. A suture sleeve (not shown) can be secured to an implantable lead 282 by bonding or otherwise securing the suture sleeve over the radial projection 280. Similar to the configuration discussed with reference to FIG. 2G, the suture sleeve can be provided with suture receiving tracks, such as those shown and discussed above with reference to FIG. 1B, by way of the securement of a suture sleeve over the radial projection 280. The radial projection 280 can have a notched spiral configuration that can be used in relation to embodiments of the present invention. In certain embodiments, the spiral shape can be provided with a taper. The taper can occur from both ends of the radial projection 280 such that the centermost portion is raised apart from the implantable lead 282 as compared to the end portions of the radial projection 276.

Figure 2I:
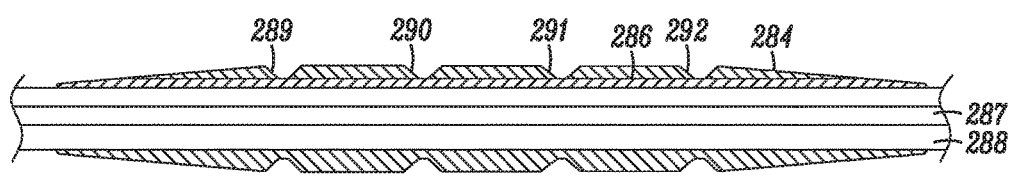
FIG. 2I shows a cross sectional view, taken from FIG. 1B as an alternative embodiment to those of FIGS. 2A-C and FIG. 2F, of a suture sleeve secured to a lead by an adhesive layer.

FIG. 2I shows a cross sectional view, taken from FIG. 1B as an alternative embodiment to those of FIGS. 2A-F, of a suture sleeve 284 secured to a lead 288 by an adhesive layer 286. The cross sectional view can represent, for example, a cross-sectional view taken from the line A-A shown in FIG. 1B. The cross-sectional view in FIG. 2I shows the cross-sectional aspects of the suture sleeve 284 and a lumen 287 of the implantable lead 288, however, the other internal components (e.g., electrical components) of the implantable lead 288 are omitted. As shown, the suture sleeve 284 may be directly attached to the implantable lead 288 via the adhesive layer 286. The suture sleeve 284 may be positioned along the implantable lead 288, and the adhesive layer 286 may be provided between the suture sleeve 284 and the implantable lead 288. The adhesive layer 286 may be provided along a portion of the suture sleeve 284, as shown in FIG. 2I, or the adhesive layer 286 may be provided along the circumference of the suture sleeve 284. The adhesive layer 286 may be a medical adhesive. The outer surface of the implantable lead 288 may be treated, prior to securing the suture sleeve 284 thereto, to increase the ability of the surface to non-removeably secure the suture sleeve 284. The suture sleeve 284 may then be bonded to the implantable lead 288 via the adhesive layer 286. More specifically, the outer surface of the implantable lead 288 may be plasma treated (or otherwise cleaned), and the suture sleeve 284 may be bonded thereto via the adhesive layer 286. In certain instances, the adhesive layer 286 is as flexible or more flexible than the suture sleeve 284. In addition, the adhesive layer 286 may have a first durometer, and the suture sleeve 284 may have a second durometer. The first durometer may be lower than the second durometer. In addition, the suture sleeve 284 may include suture one or more receiving tracks 289, 290, 291, 292 that may hold a suture to secure the implantable lead 288 in place within the body. The tracks 289, 290, 291, 292 may be formed as a continuous ring around the exterior surface of the suture sleeve 284.

In each of the arrangements shown in FIGS. 2A-2I, the radial projections may be attached to the implantable lead by over molding or pre-molding the radial projection, and subsequently bonding (e.g., heat bonding, polycin vorite bonding) the radial projection to the implantable lead. In certain other embodiments, the suture sleeve may be molded and subsequently bonded to the implantable lead using a medical adhesive after priming the implantable lead with a bonding agent, and plasma treating the implantable lead. In these such embodiments, the radial projection can be the medical adhesive. Thus, the radial projection can be provided with a low profile, and not include raised portions described herein.

In addition, the suture sleeve and the radial projections can be formed of various different materials. In certain embodiments, the suture sleeve and the radial projections are formed of different materials. For instance, the suture sleeve can be formed of silicone, and the radial projections can be formed of polycin vorite (PCV), polyurethane, or polycarbonate. Other suitable materials are also contemplated.

Figure 3:
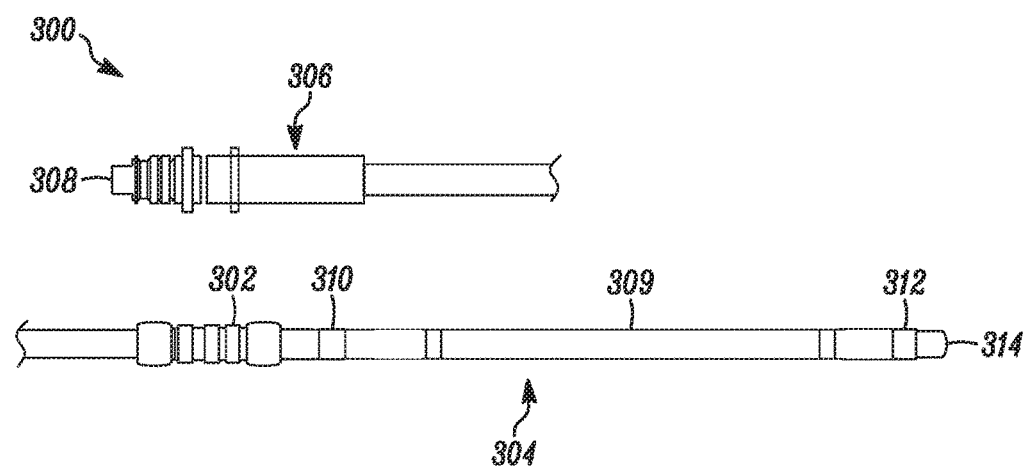
FIG. 3 shows a schematic illustration of an implantable medical lead having a suture sleeve mounted thereon.

FIG. 3 shows a schematic illustration of an implantable medical lead 300 including a suture sleeve 302. The implantable medical lead 300 has a distal region 304, a proximal region 306, and an intermediate region therebetween. The intermediate region is not shown in FIG. 3 (as is represented by the fragmented depiction of the lead 300). The proximal region 306 includes a connector 308 for the implantable medical lead 300 to connect to a pulse generator (as described, for example, with reference to FIG. 1A). The suture sleeve 302 is arranged at the distal region 304 of the implantable medical lead 300, along with an electrode 309, and a first sense electrode 310, and a second sense electrode 312. The electrode 309 is configured to provide a stimulation pulse to a patient's heart. The electrode 309 can provide the stimulation in response to the first sense electrodes 310 and the second sense electrode 312 determining that the patient's heart has an irregular rhythm.

The second sense electrode 312 is provided nearer a distal end tip of the implantable medical lead 300 than the first sense electrodes 310, which is provided between the suture sleeve 302 and the electrode 309. The gap between the suture sleeve 302 and the first sense electrode 310 is between 2 mm and 15 mm. In the embodiment shown in FIG. 3, the gap between the suture sleeve 302 and the first sense electrode 310 is 7.5 mm. The suture sleeve 302 is secured on the implantable medical lead 300 such that the suture sleeve 302 will not cover the first sense electrode 310 and thereby interfere with the function of the first sense electrode 310. The suture sleeve 302 is secured to the implantable medical lead 300 using radial projections, as shown and discussed above with reference to FIGS. 2A-2I.

The suture sleeve 302 is secured to the implantable medical lead 300, for example, by sliding the suture sleeve 302 along the implantable medical lead 300 from the proximal region 306 to the distal region 304. The suture sleeve 302 has lumen that an interior surface of the suture sleeve 302, and that is sized to receive the implantable medical lead 300. The radial projection, used to secure the suture sleeve 302 to the implantable medical lead 300, is bonded to the implantable medical lead 300 at a position nearer the proximal region 306 than the first sense electrode 310. The suture sleeve 302 is slid along the length of the implantable medical lead 300 until reaching the radial projection. The suture sleeve 302 can be engaged with the radial projection by forcing the suture sleeve 302 over the structure.

The suture sleeve 302 can also be snap-fit to the secured to the implantable medical lead 300 by snap-fitting the suture sleeve 302 over the radial projection (as shown in FIG. 2C), or the suture sleeve 302 can be directly molded to the implantable medical lead 300. In addition, the rivet features, as described above with reference to FIG. 2B, or radial protrusions may be formed using a high durometer epoxy resin. The rivets or radial projections may be formed by filling the voids in a suture sleeve with epoxy, and then allowing it to cure and harden to form the rivets or radial projections.

The suture sleeves described above and otherwise wherein can be modified in view of any other embodiment presented herein, as the present application provides examples of various features that are selectively useable together and are not presented in a restrictive sense. Various modifications and additions can be made to the embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

We claim:

1. An implantable medical device comprising:
an implantable lead having a distal region, a proximal region, and an intermediate region therebetween;
a suture sleeve having an interior surface defining a lumen of the suture sleeve, the lumen receiving the implantable lead, the suture sleeve comprising an exterior surface that defines at least one suture receiving track and at least one indentation along the interior surface of the suture sleeve; and
an engagement feature arranged on the implantable lead and configured to non-removeablely secure the suture sleeve to the implantable lead and the engagement feature comprises at least one radial projection having an upper surface, a lower surface, and sidewalls, the upper surface and the sidewalls being configured to provide a mechanical stop for the suture sleeve and engage the at least one indentation to secure the suture sleeve to the implantable lead.

2. The medical device of claim 1, wherein the at least one radial projection comprises opposing sidewalls configured to engage the at least one indentation to secure the suture sleeve to the implantable lead.

* * * * *